(12) United States Patent
Adachi et al.

(10) Patent No.: US 11,534,139 B2
(45) Date of Patent: Dec. 27, 2022

(54) ULTRASONIC DIAGNOSTIC DEVICE AND ULTRASONIC DIAGNOSTIC SYSTEM

(71) Applicant: SOCIONEXT INC., Kanagawa (JP)

(72) Inventors: Naoto Adachi, Yokohama (JP); Naoto Yoneda, Yokohama (JP); Mari Kobayashi, Yokohama (JP); Masaya Tamamura, Yokohama (JP); Amane Inoue, Yokohama (JP)

(73) Assignee: SOCIONEXT INC., Kanagawa (JP)

( * ) Notice: Subject to any disclaimer, the term of this patent is extended or adjusted under 35 U.S.C. 154(b) by 0 days.

(21) Appl. No.: 16/843,445

(22) Filed: Apr. 8, 2020

(65) Prior Publication Data

US 2020/0229790 A1     Jul. 23, 2020

Related U.S. Application Data

(63) Continuation of application No. PCT/JP2017/037497, filed on Oct. 17, 2017.

(51) Int. Cl.
*A61B 8/00*      (2006.01)
*A61B 8/08*      (2006.01)

(52) U.S. Cl.
CPC .......... *A61B 8/4411* (2013.01); *A61B 8/4455* (2013.01); *A61B 8/4472* (2013.01); *A61B 8/4477* (2013.01); *A61B 8/461* (2013.01); *A61B 8/56* (2013.01); *A61B 8/5207* (2013.01)

(58) Field of Classification Search
CPC ... A61B 8/4411; A61B 8/4455; A61B 8/4472; A61B 8/4477; A61B 8/461; A61B 8/5207; A61B 8/56
See application file for complete search history.

(56) References Cited

U.S. PATENT DOCUMENTS

| 5,617,866 A | 4/1997 | Marian, Jr. |
| 9,192,961 B2 | 11/2015 | Takahashi |
| 2010/0249600 A1 | 9/2010 | Kudoh et al. |
| 2012/0101389 A1* | 4/2012 | Tanabe ................ A61B 8/4438 600/459 |

(Continued)

FOREIGN PATENT DOCUMENTS

| CN | 103379863 A | 10/2013 |
| JP | H01-181851 A | 7/1989 |

(Continued)

OTHER PUBLICATIONS

International Search Report of International Application No. PCT/JP2017/037497 dated Nov. 28, 2017; with English translation.

(Continued)

*Primary Examiner* — Yi-Shan Yang
*Assistant Examiner* — Alexei Bykhovski
(74) *Attorney, Agent, or Firm* — McDermott Will & Emery LLP (57) ABSTRACT

An ultrasonic diagnostic device includes a probe configured to transmit an ultrasonic wave to a subject and to receive the ultrasonic wave reflected by the subject; an image processor configured to convert ultrasonic image data based on the ultrasonic wave received by the probe, into digital data; a main body configured to output the digital data output from the image processor; and a connector configured to electrically connect and disconnect the image processor with respect to the main body.

4 Claims, 8 Drawing Sheets

(56) References Cited

U.S. PATENT DOCUMENTS

2013/0253327 A1* 9/2013 Ko .................. A61B 8/4444
                                                    600/459
2016/0238563 A1* 8/2016 Lee .................. A61B 8/4411

FOREIGN PATENT DOCUMENTS

| JP | 2001-508314 A | 6/2001 |
| JP | 2009-060992 A | 3/2009 |
| JP | 2010-227356 A | 10/2010 |
| JP | 2010-227357 A | 10/2010 |
| JP | 2012-090712 A | 5/2012 |
| JP | 2013-085688 A | 5/2013 |
| JP | 2013-172800 A | 9/2013 |
| JP | 2013-543785 A | 12/2013 |

OTHER PUBLICATIONS

Written Opinion of the International Searching Authority of International Application No. PCT/JP2017/037497 dated Nov. 28, 2017; with English translation of relevant part.

Notification of the First Office Action dated Apr. 20, 2022 issued in the corresponding Chinese Patent Application No. 201780095746.7, with English translation.

* cited by examiner

ULTRASONIC DIAGNOSTIC DEVICE AND ULTRASONIC DIAGNOSTIC SYSTEM

CROSS-REFERENCE TO RELATED APPLICATIONS

This U.S. non-provisional application is a continuation application of and claims the benefit of priority under 35 U.S.C. § 365(c) from PCT International Application PCT/JP2017/037497 filed on Oct. 17, 2017, designated the U.S., the entire contents of which are incorporated herein by reference.

TECHNICAL FIELD

The present disclosure relates to an ultrasonic diagnostic device and an ultrasonic diagnostic system.

BACKGROUND ART

Conventionally, ultrasonic diagnostic devices have been known that emit ultrasonic waves to a subject, and receive reflected waves from the subject to obtain ultrasonic images. Also, when an ultrasonic image is captured by an ultrasonic diagnostic device, it has been known that the frequency of the ultrasonic wave and the shape of the probe to transmit and receive the ultrasonic wave differ depending on the part to be observed.

For this reason, conventionally, an ultrasonic diagnostic device has been known in which a tip part (probe) including a group of acoustic elements to transmit and receive ultrasonic waves according to target parts can be attached to and detached from the main body of the device that is connected with the tip part via a cable.

See, for example, the following patent documents:
Japanese Patent No. 6067966
Japanese Patent No. 6024120

Connection between the probe and the main body of the device requires multiple channels of signal lines for transmission and reception of ultrasonic waves. Also, a reflected wave of the ultrasonic wave received by the probe is a reflected signal from a living body, and hence, is a very weak analog signal.

For this reason, if attempting to maintain the image quality of ultrasonic images, the cable connecting the probe and the main body of the device would become very expensive, difficult to handle, and difficult to attach and detach the probe with respect to the main body of the device.

SUMMARY

The disclosed techniques relate to an ultrasonic diagnostic device that includes a probe configured to transmit an ultrasonic wave to a subject and to receive the ultrasonic wave reflected by the subject; an image processor configured to convert ultrasonic image data based on the ultrasonic wave received by the probe, into digital data; a main body configured to output the digital data output from the image processor; and a connector configured to electrically connect and disconnect the image processor with respect to the main body.

EMBODIMENTS OF THE INVENTION

According to an embodiment, it is possible to attach and detach a probe easily.

First Embodiment

Figure 1:
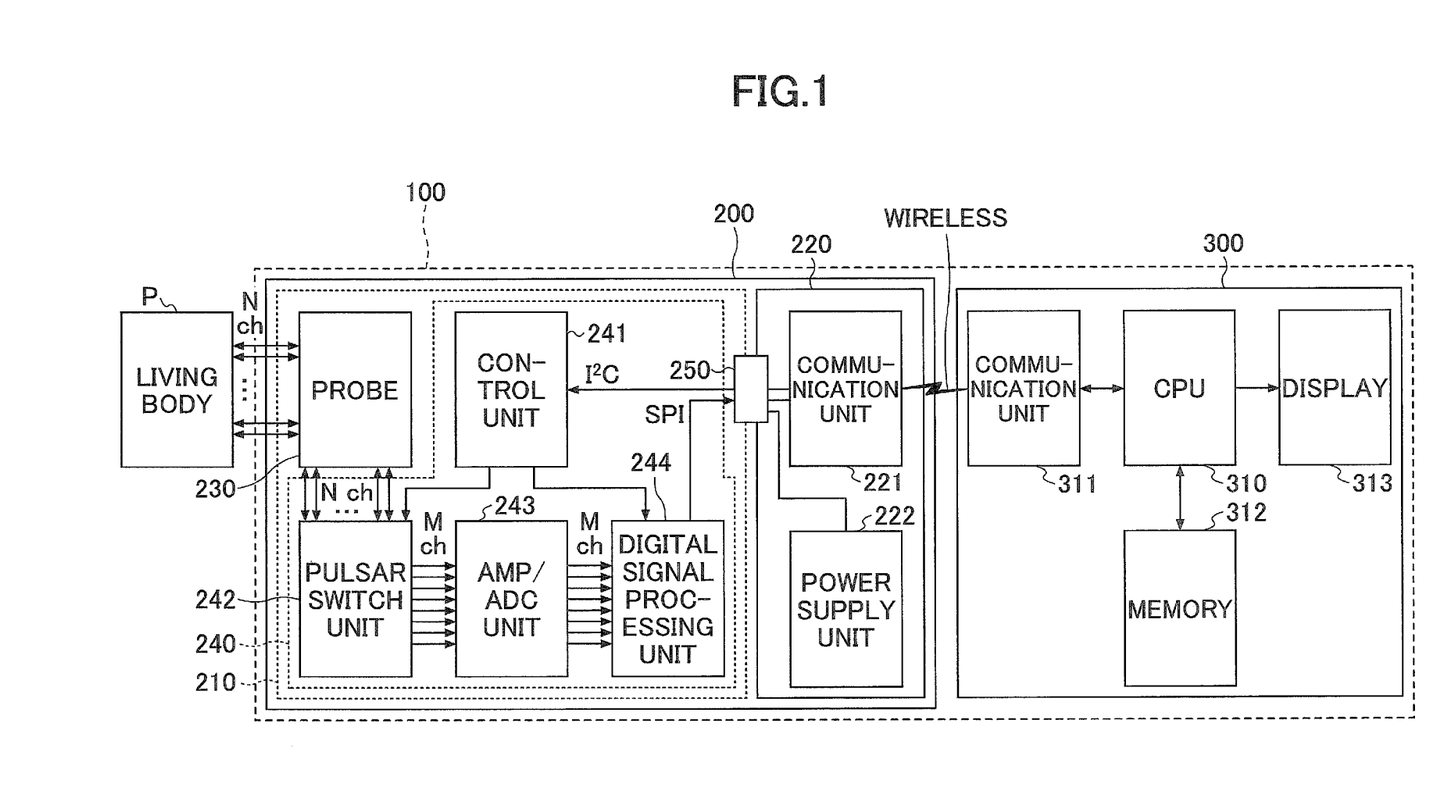
FIG. 1 is a diagram illustrating a configuration of an ultrasonic diagnostic system of a first embodiment.

In the following, a first embodiment will be described with reference to the drawings. FIG. 1 is a diagram illustrating a configuration of an ultrasonic diagnostic system of a first embodiment.

In the present embodiment, an ultrasonic diagnostic system 100 includes an ultrasonic diagnostic device 200 and a terminal device 300. The ultrasonic diagnostic device 200 and the control device 300 communicate wirelessly.

First, the ultrasonic diagnostic device 200 of the present embodiment will be described. The ultrasonic diagnostic device 200 of the present embodiment includes an ultrasonic image obtaining unit 210 including a probe 230, and a main body part 220.

The ultrasonic image obtaining unit 210 and the main body part 220 of the present embodiment are electrically connected or disconnected by a connector 250. In other words, in the ultrasonic diagnostic device 200 of the present embodiment, the ultrasonic image obtaining unit 210 including the probe 230 can be attached to or detached from the main body part 220.

In the present embodiment, the ultrasonic image obtaining unit 210 includes the probe 230 and an image processing unit 240. The probe 230 transmits (emits) an ultrasonic wave to a living body (subject) P and receives the reflected wave.

The image processing unit 240 includes a control unit 241; a pulsar switch unit 242; an AMP (amplifier)/ADC (analog to digital converter) unit 243; and a digital signal processing unit 244, causes the probe 230 to transmit an ultrasound, generates an ultrasonic image data based on the reflected wave (ultrasound) received by the probe 230, and outputs the data to the main body part 220.

The control unit 241 controls the entire ultrasonic diagnostic device 200. Also, the control unit 241 is connected to the connector 250 by an I²C (I-squared-C) or the like. A signal output from the main body part 220 is input into the control unit 241 via the connector 250.

The pulsar switch unit 242 selects the probe 230 by a switch part, and transmits a pulse signal to the probe 230, to cause the probe 230 to emit an ultrasonic wave to the living body P.

When irradiated with the ultrasonic wave, the living body P reflects the ultrasonic wave at a boundary where the acoustic impedance differs. The reflected wave reflected from the living body P is received by the probe 230, and is output to the AMP/ADC unit 243 selected by the switch part of the pulsar switch unit 242.

The AMP/ADC unit 243 amplifies the reflected wave of the ultrasonic wave output from the pulsar switch unit 242 by the amplifier (AMP), converts the amplified wave into a digital signal by the ADC, and outputs the signal to the digital signal processing unit 244.

The digital signal processing unit 244 performs various processing on the digital signal output from the AMP/ADC unit 243 to obtain ultrasonic image data, and output the data to the main body part 220 via the connector 250.

Specifically, the processing performed by the digital signal processing unit 244 includes a process of aligning the delay from the time when the reflected wave was output from the pulsar switch unit 242; a process of averaging (in-phase addition); a process of gain correction that takes into account the attenuation in the living body P; and an envelope process for obtaining the brightness information.

The digital signal processing unit 244 is connected to the connector 250 by SPI (Serial Peripheral Interface) or the like, to transmit ultrasonic image data to the main body part 220 by SPI.

The main body part 220 of the present embodiment includes a wireless communication unit 221 and a power supply unit 222, and is connected to the ultrasonic image obtaining unit 210 via the connector 250.

The wireless communication unit 221 performs communication with the terminal device 300. Specifically, the wireless communication unit 221 performs wireless communication with the terminal device 300, for example, according to a standard such as Wi-Fi. Note that the standard used for the wireless communication is not limited to Wi-Fi, and may be another standard.

The wireless communication unit 221 is connected to the connector 250, to receive a signal transmitted from the terminal device 300. Specifically, the wireless communication unit 221 receives, for example, an emission command of an ultrasonic wave or the like from the terminal device 300.

Also, the wireless communication unit 221 of the present embodiment transmits a signal output from the ultrasonic image obtaining unit 210 to the terminal device 300. Specifically, the wireless communication unit 221 transmits ultrasonic image data to the terminal device 300.

The power supply unit 222 may be, for example, a rechargeable secondary battery or the like to provide power to the units of the ultrasonic diagnostic device 200.

In this way, in the present embodiment, the ultrasonic diagnostic device 200 causes the ultrasonic image obtaining unit 210 to digitize ultrasonic image data, and then, output the data as digital signals to the main body part 220. In other words, according to the present embodiment, the ultrasonic image data to be transferred between the ultrasonic image obtaining unit 210 and the main body part 220 is constituted with digital signals (digital data).

Also, in the present embodiment, signals are transferred using buses such as I²C and SPI; therefore, the interface between the ultrasonic image obtaining unit 210 and the main body part 220 can be implemented with several digital signal lines. Therefore, according to the present embodiment, the connector 250 connecting the ultrasonic image obtaining unit 210 and the main body part 220 can have a simple configuration.

For this reason, according to the present embodiment, with such a simple configuration, the ultrasonic image obtaining unit 210 and the main body part 220 can be electrically connected or disconnected. Also, according to the present embodiment, the signal transferred via the connector 250 is a digital signal of ultrasonic image data; therefore, the image quality is not deteriorated when connecting or disconnecting the ultrasonic image obtaining unit 210 with respect to the main body part 220, and the image quality of the ultrasonic image data can be maintained.

Next, the terminal device 300 of the present embodiment will be described. The terminal device 300 of the present embodiment includes a CPU 310, a wireless communication unit 311, a memory 312, and a display 313.

The CPU 310 controls the overall operations of the terminal device 300. The wireless communication unit 311 receives a signal transmitted from the ultrasonic diagnostic device 200. Specifically, the wireless communication unit 311 receives ultrasonic image data transmitted from the ultrasonic diagnostic device 200.

The memory 312 stores ultrasonic image data received by the wireless communication unit 311 and data obtained as a result of calculation by the CPU 310.

The display 313 displays ultrasonic image data and the like received from the ultrasonic diagnostic device 200.

Note that the terminal device 300 of the present embodiment may be, for example, a tablet-type terminal device, and in that case, the display 313 may include a touch panel or the like.

In the ultrasonic diagnostic system 100 of the present embodiment, the ultrasonic diagnostic device 200 transmits ultrasonic image data to the terminal device 300 by wireless communication. Therefore, according to the present embodiment, when scanning the living body P by the ultrasonic diagnostic device 200, the motion of the operator of the ultrasonic diagnostic device 200 is not hindered by a communication cable or the like.

Next, with reference to FIG. 2, attachment and detachment of the ultrasonic image obtaining unit 210 (probe 230) with respect to the main body part 220 in the ultrasonic diagnostic device 200 of the present embodiment will be described.

Figure 2:
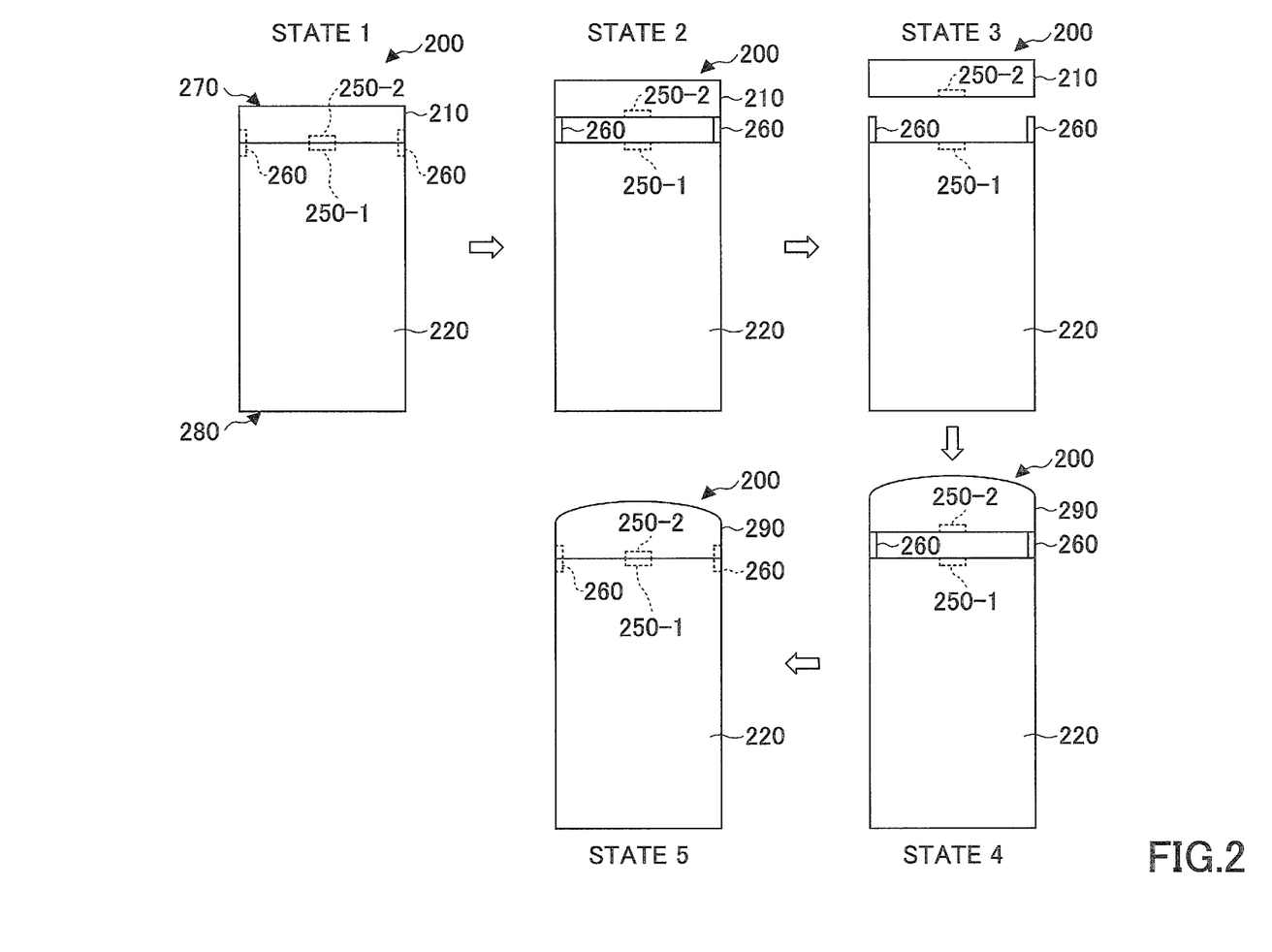
FIG. 2 is a diagram illustrating attachment and detachment of a probe in an ultrasonic diagnostic device of a first embodiment.

FIG. 2 is a diagram illustrating attachment and detachment of the probe in the ultrasonic diagnostic device of the first embodiment.

State 1 illustrated in FIG. 2 corresponds to a state in which the ultrasonic image obtaining unit 210 and the main body part 220 are electrically connected via the connector 250.

In the ultrasonic diagnostic device 200 of the present embodiment, a circuit board having the image processing unit 240 mounted and a circuit board having the main body part 220 mounted are contained in separate housings 270 and 280, respectively. In addition, the circuit board having the image processing unit 240 mounted is provided with a male connector 250-1 as the connection part, the circuit board having the main body part 220 mounted is provided with a female connector 250-2 as the connection part. The connector 250-1 and the connector 250-2 can be plugged into and pulled apart from each other.

In the present embodiment, by plugging the connector 250-1 into the connector 250-2, the image processing unit 240 (ultrasonic image obtaining unit 210) and the main body part 220 are electrically connected, and the housing 270 and the housing 280 are coupled. Note that in the above description, although the connector 250-1 is a male type and the connector 250-2 is a female type, the shape of the connector 250 is not limited as such.

Also, in the present embodiment, an attaching/detaching mechanism 260 is provided for making the housing 270 and the housing 280 attachable and detachable.

The attaching/detaching mechanism 260 is secured to, for example, the housing 280 so that the housing 270 can be held in a state of being coupled with the housing 280, in a state where the electrical connection between the ultrasonic image obtaining unit 210 and the main body part 220 via the connector 250 is cut off. Also, the attaching/detaching mechanism 260 enables to remove the housing 270 from the housing 280.

State 2 illustrated in FIG. 2 corresponds to a state in which the connector 250-1 and the connector 250-2 are separated; the electrical connection between the ultrasonic image obtaining unit 210 and the main body part 220 is cut off; and the housing 270 and the housing 280 are still coupled via the attaching/detaching mechanism 260.

In this way, in the present embodiment, it is possible to realize a state in which the electrical connection between the ultrasonic image obtaining unit 210 and the main body part 220 is cut off, and yet the housing 270 is coupled with the housing 280.

Therefore, according to the present embodiment, the loss of the housing 270 containing the ultrasonic image obtaining unit 210 can be prevented. In other words, the loss of the probe 230 removed from the main body part 220 can be prevented.

State 3 illustrated in FIG. 2 corresponds to a state in which the housing 270 is detached from the attachment/detaching mechanism 260. In other words, state 3 corresponds to a state in which the housing 270 containing the ultrasonic image obtaining unit 210 is detached from the ultrasonic diagnostic device 200.

In the present embodiment, the housing 270 can be completely detached as in State 3. Therefore, in the present embodiment, after having the housing 270 detached, a housing 290 that contains another ultrasonic image obtaining unit having a probe of a different type from the probe 230, can be attached to the main body part 220, as illustrated in States 4 and 5.

State 4 corresponds to a state in which the housing 290 is attached to the attaching/detaching mechanism 260. Note that it is assumed that a circuit board contained in the housing 290 is provided with a connector 250-1.

State 4 corresponds to a state in which the housing 280 and the housing 290 are coupled via the attachment/detaching mechanism 260, and the ultrasonic image obtaining unit contained in the housing 290 and the main body part 220 are not electrically connected.

State 5 corresponds to a state in which the ultrasonic image obtaining unit contained in the housing 290 and the main body part 220 are electrically connected, and the housing 280 and the housing 290 are coupled via the attachment/detaching mechanism 260. In other words, State 5 corresponds to a state in which the ultrasonic image obtaining unit 210 including the probe 230 is replaced with an ultrasonic image obtaining unit including another probe. In this way, according to the present embodiment, the probe can be replaced depending on the application of the ultrasonic diagnostic device 200. Note that various types and shapes are available for the probes, which may be linear, convex, sector, and the like.

In the present embodiment, the attaching/detaching mechanism 260 may be configured such that, for example, the connector 250-2 is pulled apart from the connector 250-1 by pulling the housing 270 away from the housing 280, and yet the connection between the housing 270 and the housing 280 is maintained. Also, in the present embodiment, the attaching/detaching mechanism 260 may be configured such that State 3, in which the housing 270 is detached from the attaching/detaching mechanism 260, can be reached by further pulling the housing 270 away from the housing 280 in State 2.

Also, the ultrasonic diagnostic device 200 of the present embodiment may have the attachment/detaching mechanism 260 configured such that State 1 transitions to State 2, for example, in response to an operation performed on an operational member or the like provided on the housing 270 or the housing 280.

Also, in the present embodiment, the attaching/detaching mechanism 260 may be configured such that, for example, in State 2, by pushing the housing 270 so as to be closer to the housing, the connector 250-2 is plugged into the connector 250-1, and the housing 270 is coupled with the housing 280.

In this way, according to the present embodiment, the probe 230 can be easily attached and detached with a simple configuration.

Second Embodiment

In the following, a second embodiment will be described with reference to the drawings. An ultrasonic diagnostic system in the second embodiment differs from the first embodiment only in a point that communication between the ultrasonic diagnostic device and the terminal device is performed by wire, not wirelessly. Therefore, in the following description of the second embodiment, only the differences from the first embodiment will be described, and those elements having the same functional configurations as in the first embodiment are assigned the same symbols as used in the description of the first embodiment, and the description will be omitted.

Figure 3:
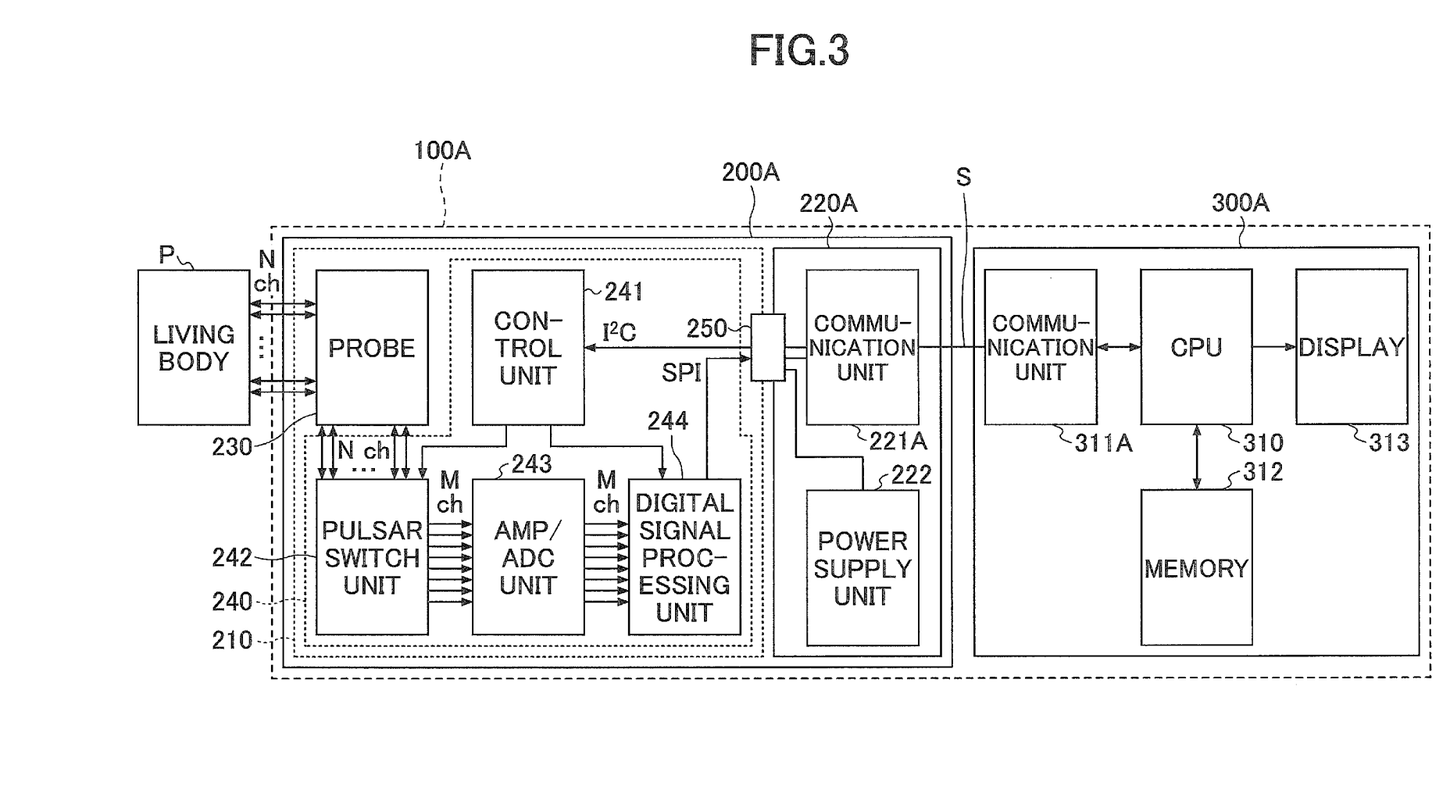
FIG. 3 is a diagram illustrating a configuration of an ultrasonic diagnostic system of a second embodiment.

FIG. 3 is a diagram illustrating a configuration of an ultrasonic diagnostic system of the second embodiment. In the present embodiment, an ultrasonic diagnostic system 100A includes an ultrasonic diagnostic device 200A and a terminal device 300A. In the ultrasonic diagnostic system 100A, the ultrasonic diagnostic device 200A and the terminal device 300A communicate with each other by wire.

The ultrasonic diagnostic device 200A of the present embodiment includes an ultrasonic image obtaining unit 210 and a main body part 220A. The main body part 220A includes a communication unit 221A and a power supply unit 222.

The communication unit 221A of the present embodiment is connected to a connector 250, and transmits ultrasonic image data received from the ultrasonic image obtaining unit 210 to the terminal device 300A through communication by wire. Note that the communication by wire may be performed by using any communication scheme as long as the scheme can be applied to communication between the ultrasonic diagnostic device 200A and the terminal device 300A.

The terminal device 300A of the present embodiment includes a CPU 310, a communication unit 311A, a memory 312, and a display 313. The communication unit 311A of the present embodiment communicates with the ultrasonic diagnostic device 200A by wire.

In the ultrasonic diagnostic system 100A of the present embodiment, even in the case where the ultrasonic diagnostic device 200A and the terminal device 300A communicate by wire, the same effects as in the first embodiment can be achieved.

Third Embodiment

In the following, a third embodiment will be described with reference to the drawings. An ultrasonic diagnostic device in the third embodiment differs from the first embodiment, in that it has a display. Therefore, in the following description of the third embodiment, only the differences from the first embodiment will be described, and those elements having the same functional configurations as in the first embodiment are assigned the same symbols as used in the description of the first embodiment, and the description will be omitted.

Figure 4:
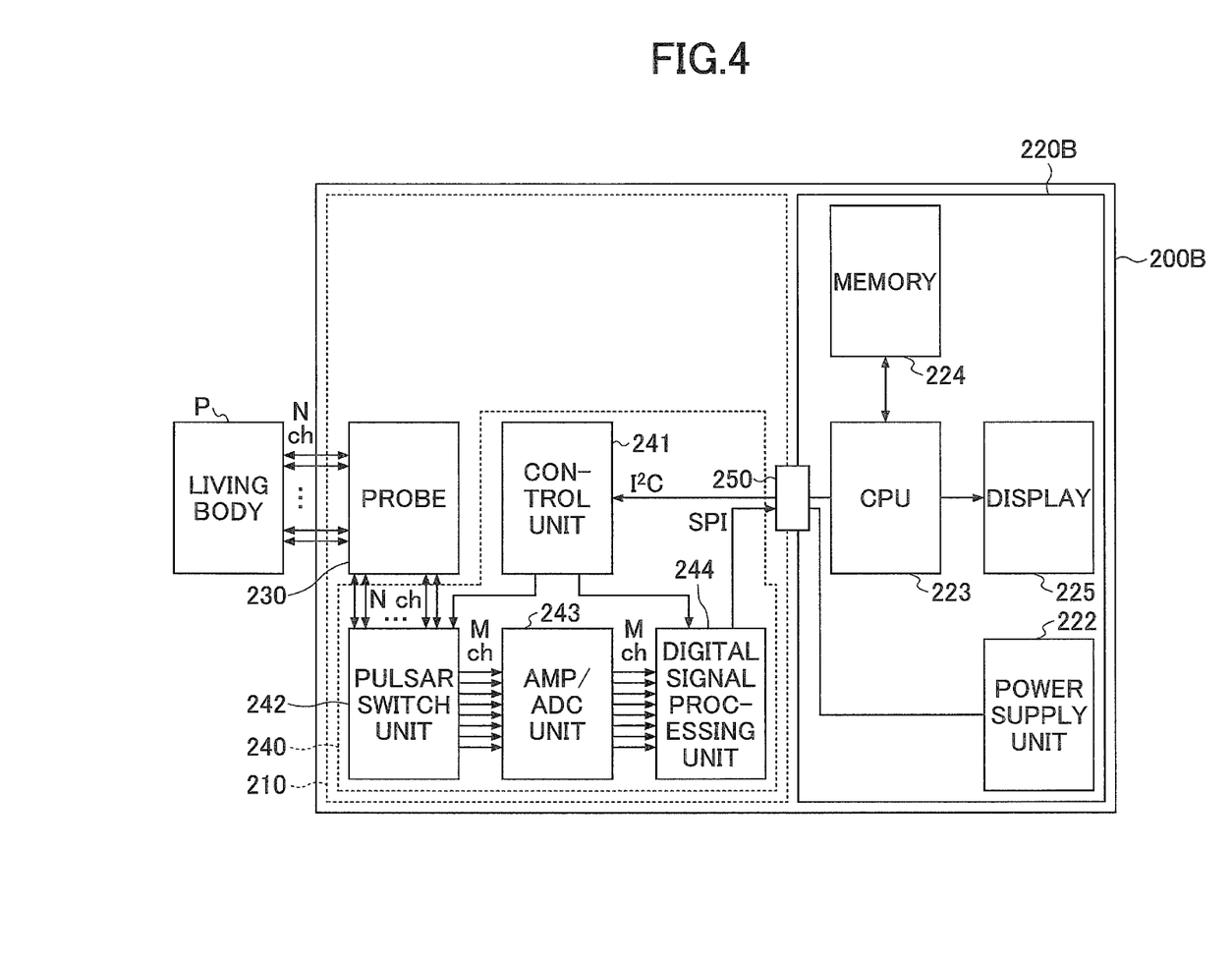
FIG. 4 is a diagram illustrating a configuration of an ultrasonic diagnostic system of a third embodiment.

FIG. 4 is a diagram illustrating a configuration of an ultrasonic diagnostic system of the third embodiment. An ultrasonic diagnostic device 200B of the present embodiment includes an ultrasonic image obtaining unit 210 and a main body part 220B.

The main body part 220B of the present embodiment includes a power supply unit 222, a CPU 223, a memory 224, and a display 225.

The CPU 223 controls operations of the main body part 220B. Specifically, the CPU 223 is connected to a connector 250, to receive, as input, ultrasonic image data output from the ultrasonic image obtaining unit 210. The CPU 223 may display the ultrasonic image data on the display 225 in response to receiving the ultrasonic image data as input.

The memory 224 stores ultrasonic image data obtained by the CPU 223 and data obtained as a result of calculation by the CPU 223.

The display 225 displays ultrasonic image data or the like obtained by the CPU 223. Also, the display 225 may display various information items on operations of the ultrasonic diagnostic device 200B.

In this way, according to the present embodiment, providing the display 225 in the ultrasonic diagnostic device 200B enables to display ultrasonic image data without communicating with the terminal device 300. In other words, according to the present embodiment, the terminal device 300 for displaying ultrasonic image data is not required.

Fourth Embodiment

In the following, a fourth embodiment will be described with reference to the drawings. An ultrasonic diagnostic device of the fourth embodiment differs from the first embodiment, in that two probes can be connected to the main body part 220. Therefore, in the following description of the fourth embodiment, only the differences from the first embodiment will be described, and those elements having the same functional configurations as in the first embodiment are assigned the same symbols as used in the description of the first embodiment, and the description will be omitted.

Figure 5:
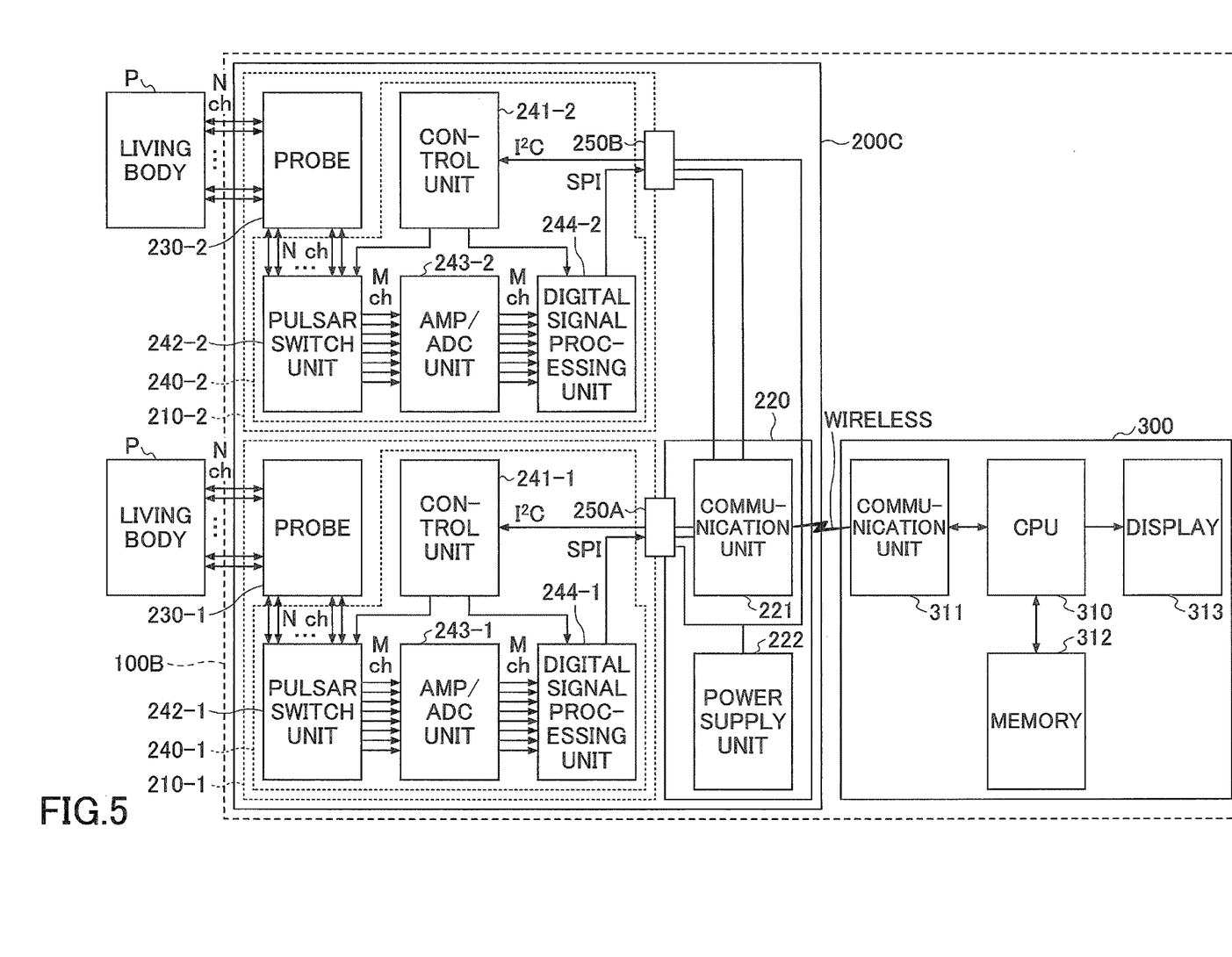
FIG. 5 is a diagram illustrating a configuration of an ultrasonic diagnostic system of the fourth embodiment.

FIG. 5 is a diagram illustrating a configuration of an ultrasonic diagnostic system of the fourth embodiment. An ultrasonic diagnostic system 100B of the present embodiment includes an ultrasonic diagnostic device 200C and a terminal device 300. In the ultrasonic diagnostic system 100B, the ultrasonic diagnostic device 200C and the terminal device 300 communicate wirelessly.

The ultrasonic diagnostic device 200C of the present embodiment includes ultrasonic image obtaining units 210-1 and 210-2, and a main body part 220B.

The ultrasonic image obtaining unit 210-1 include a probe 230-1 and an image processing unit 240-1. The ultrasonic image obtaining unit 210-2 includes a probe 230-2 and an image processing unit 240-2.

The probes 230-1 and 230-2 are of different types. Also, the image processing unit 240-1 has settings that correspond to the probe 230-1, and the image processing unit 240-2 has settings that correspond to the probe 230-2.

Also, the ultrasonic image obtaining unit 210-1 is connected to the main body part 220B via the connector 250A, and the ultrasonic image obtaining unit 210-2 is connected to the main body part 220B via the connector 250B.

In other words, in the present embodiment, a circuit board having the image processing unit 240-1 mounted is provided with a male connector 250A-1 as the connection part, and a circuit board having the image processing unit 240-2 mounted is provided with a female connector 250A-2 as the connection part.

Also, a circuit board having the main body part 220B of the present embodiment mounted is provided with a female connector 250A-2 as the connection part to be connected to the connector 250A-1, and with a female connector 250B-2 as the connection part to be connected to the connector 250B-1.

Each of the connectors 250B-1 and 250B-2 is connected to the wireless communication unit 221.

The configuration of the image processing unit 240-1 and the image processing unit 240-2 is substantially the same as that of the image processing unit 240, and hence, the description will be omitted. Also, the configuration of the main body part 220B is substantially the same as that of the main body part 220, and hence, the description will be omitted.

Next, with reference to FIG. 6, attachment and detachment of the ultrasonic image obtaining units 210-1 and 210-2 (probes 230-1 and 230-2) with respect to the main body part 220B in the ultrasonic diagnostic device 200C of the present embodiment will be described.

Figure 6:
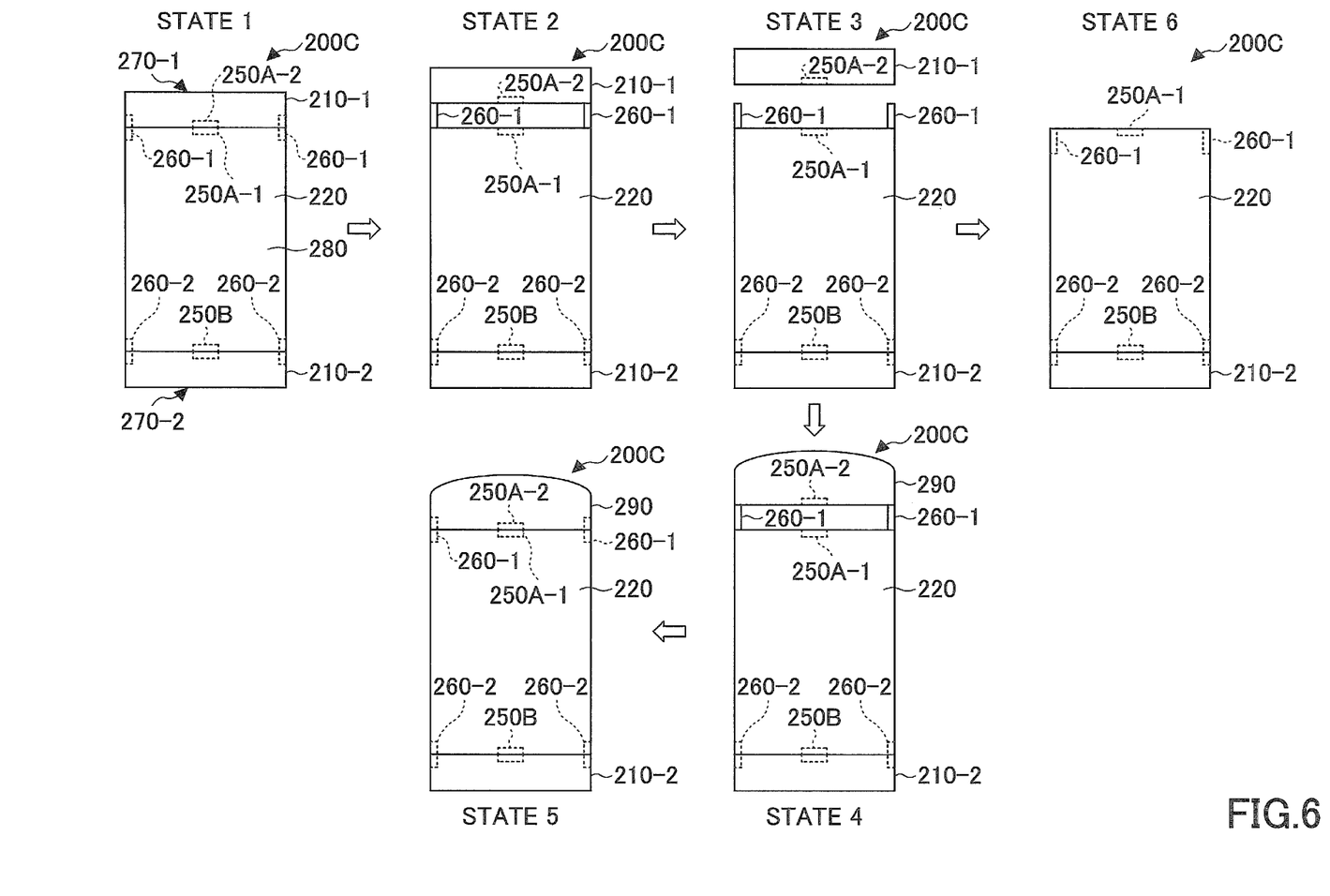
FIG. 6 is a diagram illustrating attachment and detachment of a probe in an ultrasonic diagnostic device of the fourth embodiment.

FIG. 6 is a diagram illustrating attachment and detachment of probes in the ultrasonic diagnostic device of the fourth embodiment. State 1 corresponds to a state in which a housing 270-1 containing the ultrasonic image obtaining unit 210-1 and a housing 270-2 containing the ultrasonic image obtaining unit 210-2 are attached to a housing 280 containing the circuit board having the main body part 220B mounted.

State 2 corresponds to a state in which the ultrasonic image obtaining unit 210-1 is pulled away from the main body part 220B, the connector 250A-2 is pulled apart from the connector 250A-1, and the ultrasonic image obtaining unit 210-1 is still coupled with the main body part 220B via the attaching/detaching mechanism 260-1.

In the present embodiment, for example, when transitioning from State 1 to State 2, an ultrasonic wave may be transmitted from the probe 230-2 of the ultrasonic image obtaining unit 210-2. In other words, in the ultrasonic diagnostic device 200C of the present embodiment, neither the probe 230-1 nor the probe 230-2 transmits an ultrasonic wave when the probes 230-1 and 230-2 are electrically connected to the main body part 220B. Then, when either one of the probes 230 becomes electrically disconnected from the main body part 220B, the ultrasonic diagnostic device 200C may cause the other probe 230 that is electrically connected to the main body part 220B, to transmit an ultrasonic wave.

In other words, when only one of the probes 230 is electrically connected to the main body part 220B, the ultrasonic diagnostic device 200C may cause this probe 230 to transmit an ultrasonic wave.

In this case, in the ultrasonic diagnostic device 200C, when transitioning into State 2, it becomes possible to transmit an ultrasonic wave from the probe 230-2 of the ultrasonic image obtaining unit 210-2.

States 4 and 5 in FIG. 6 are substantially the same as States 4 and 5 in FIG. 2, and hence, the description will be omitted. Also, for example, as illustrated in State 6, when the housing 270-1 is detached from the attaching/detaching mechanism 260-1, the ultrasonic diagnostic device 200C transitions into a state where the housing 280 is coupled with the housing 270-2, and the main body part 220B and the ultrasonic image obtaining unit 210-2 are electrically connected. In other words, in State 6, the ultrasonic diagnostic device 200C operates an ultrasonic wave device having the single probe 230-2.

Note that in the present embodiment, although it is assumed that an ultrasonic wave is transmitted from a probe 230 when only this probe 230 is electrically connected to the main body part 220B, it is not limited as such. The ultrasonic diagnostic device 200C of the present embodiment may select a probe to transmit an ultrasonic wave based on a command from the terminal device 300, in a state in which the probe 230-1 and the probe 230-2 are electrically connected to the main body part 220B, for example, as in State 1.

Also, in the present embodiment, for example, the ultrasonic diagnostic device 200C may have an operational member or the like provided for designating a probe 230 to transmit an ultrasonic wave, and may cause a probe 230 selected using the operational member, to transmit an ultrasonic wave.

In this way, according to the present embodiment, multiple probes 230 can be provided on a single unit of the ultrasonic diagnostic device 200C, and the probe 230 to be used may be connected to the main body part 220B and the probe 230 not to be used may be disconnected from the main body part 220B. Also, in the present embodiment, ultrasonic image data transferred between the ultrasonic image obtaining unit 210 having the probes 230 and the main body part 220B is constituted with digital signals; therefore, it is possible to attach and detach the probes 230 easily and to maintain the image quality of an ultrasonic image.

Figure 7:
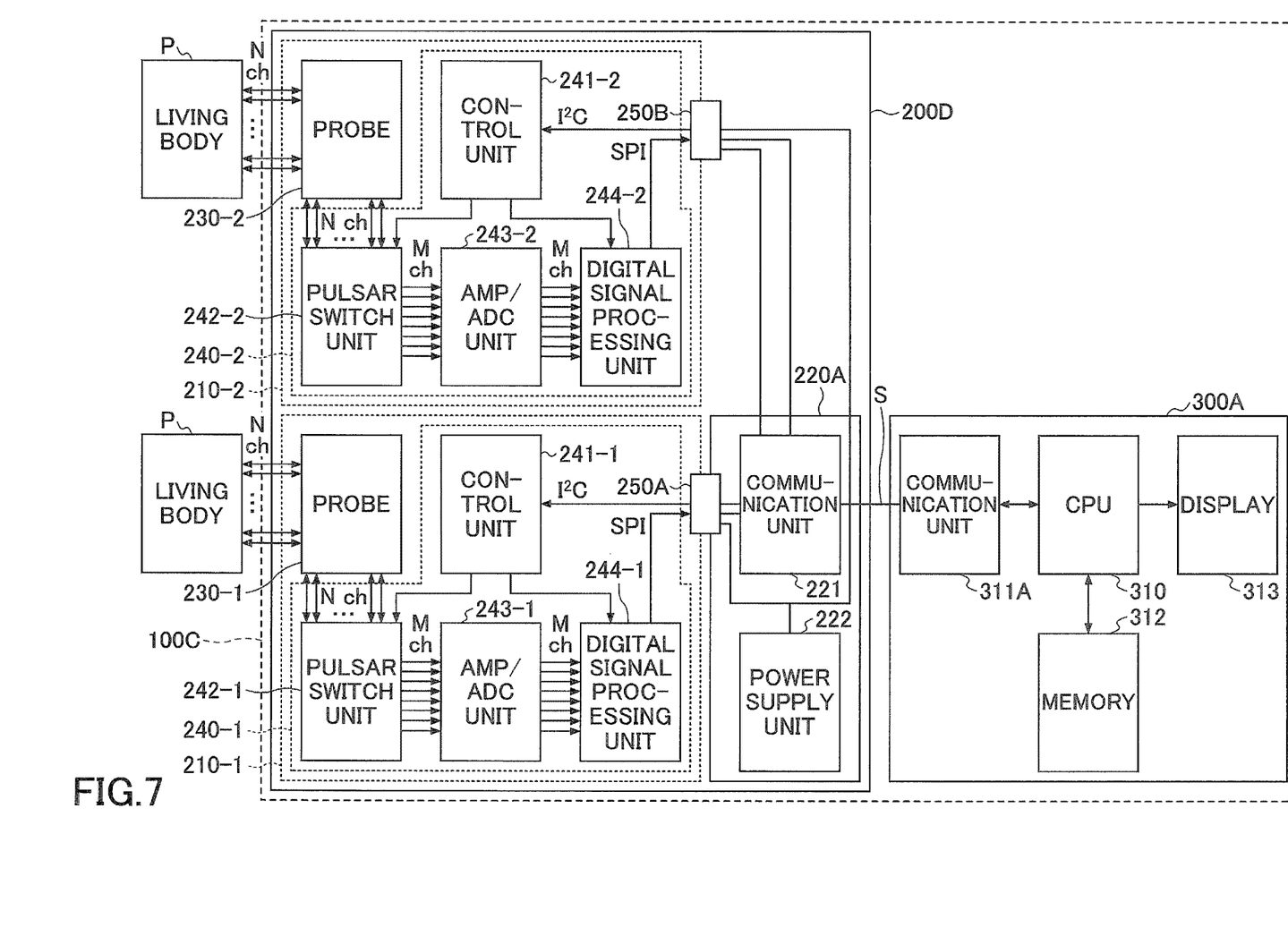
FIG. 7 is a diagram illustrating another configuration of an ultrasonic diagnostic system of the fourth embodiment.

In the following, with reference to FIGS. 7 and 8, other examples of the present embodiment will be described. FIG. 7 is a diagram illustrating another configuration of the ultrasonic diagnostic system of the fourth embodiment.

An ultrasonic diagnostic system 100C illustrated in FIG. 7 includes an ultrasonic diagnostic device 200D and a terminal device 300A. The ultrasonic diagnostic device 200D includes an ultrasonic image obtaining unit 210-1, an ultrasonic image obtaining unit 210-2, and a main body part 220A.

The ultrasonic diagnostic system 100C in the present embodiment has substantially the same configuration as the ultrasonic diagnostic system 100B in FIG. 5 except that the ultrasonic diagnostic device 200D and the terminal device 300A communicate by wire, and hence, the description will be omitted.

Figure 8:
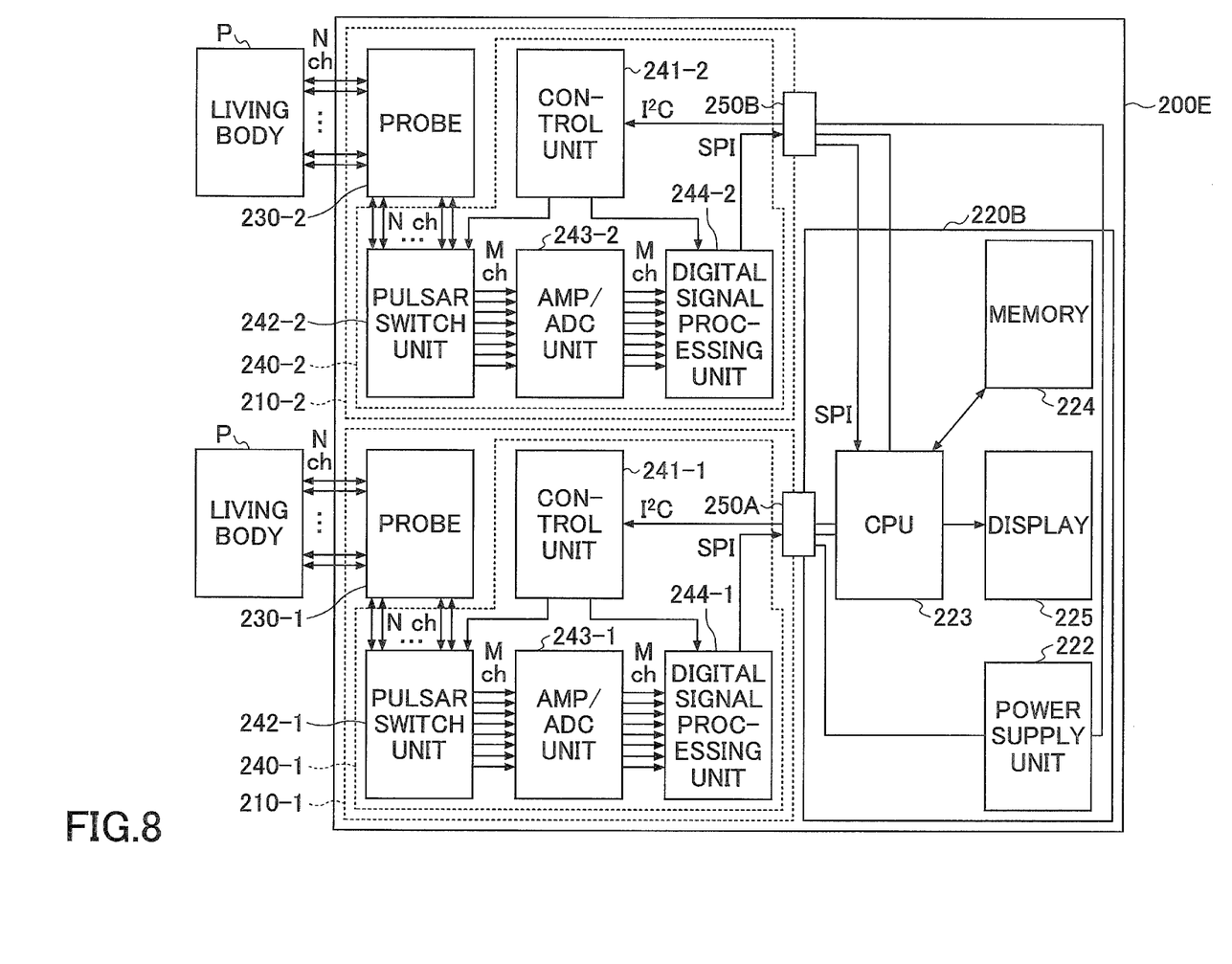
FIG. 8 is a diagram illustrating an ultrasonic diagnostic device of the fourth embodiment.

FIG. 8 is a diagram illustrating an ultrasonic diagnostic device of the fourth embodiment. An ultrasonic diagnostic device 200E of the present embodiment includes ultrasonic image obtaining units 210-1 and 210-2, and a main body part 220B. The ultrasonic image obtaining unit 210-1 is electrically connected to the main body part 220B via the connector 250A, and the ultrasonic image obtaining unit 210-2 is electrically connected to the main body part 220B via the connector 250B.

The ultrasonic diagnostic device 200E illustrated in FIG. 8 has substantially the same configuration as the ultrasonic diagnostic device 200B of the third embodiment except that the ultrasonic image obtaining unit 210-2 is provided, and hence, the description will be omitted.

As described above, according to the present embodiment, when a probe is attached to or detached from the main body part of the ultrasonic diagnostic device, it is possible to attach or detach a probe together with an ultrasonic image obtaining unit including the probe and the image processing unit to digitize ultrasonic image data. Therefore, according to the present embodiment, attaching or detaching the probe does not deteriorate the image quality of an ultrasonic image. Also, a signal line (cable) connecting the probe and the image processing unit resides within the housing containing the probe and the image processing unit; therefore, the user of the ultrasonic diagnostic device does not need to touch this signal line when attaching or detaching the probe.

Therefore, according to the present embodiment, it is possible to attach and detach the probe without deteriorating the image quality of an ultrasonic image.

As above, the present disclosure has been described based on the embodiments; note that the present inventive concept is not limited by the requirements presented in the above embodiments. In these respects, it is possible to make alterations within a range where the gist of the present inventive concept is not changed, which may be properly defined depending on the form of application.

The invention claimed is:

1. An ultrasonic diagnostic device comprising:
   a probe configured to transmit an ultrasonic wave to a subject and to receive the ultrasonic wave reflected by the subject;
   an image processor configured to convert ultrasonic image data based on the ultrasonic wave received by the probe, into digital data;
   a main body configured to output the digital data output from the image processor;
   a connector configured to electrically connect and disconnect the image processor with respect to the main body; and
   an attaching/detaching mechanism configured to attach and detach a first housing with respect to a second housing, the attaching/detaching mechanism including paired elongated structures disposed on sides of the first housing and the second housing,
   wherein the probe and the image processor are contained in the first housing, and
   wherein the main body is contained in the second housing, and
   wherein the attaching/detaching mechanism can be transitioned into:
      a first state where an electrical connection between the image processor and the main body via the connector is established, and the first housing is mechanically coupled with the second housing,
      a second state where the electrical connection between the image processor and the main body via the connector is cut off, and the first housing is mechanically coupled to the second housing, in response to the first housing being pulled in a direction away from the second housing with a predetermined force when the attaching/detaching mechanism is in the first state, and
      a third state where the electrical connection between the image processor and the main body via the connector is cut off, and the first housing is mechanically decoupled from the second housing, in response to the first housing being pulled in the direction away from the second housing with a force greater than the predetermined force when the attaching/detaching mechanism is in the second state.

2. The ultrasonic diagnostic device as claimed in claim 1, wherein when in the second state, the first housing is mechanically coupled to the second housing by the attaching/detaching mechanism such that there is a gap between the first housing and the second housing.

3. An ultrasonic diagnostic device comprising:
a probe configured to transmit an ultrasonic wave to a subject and to receive the ultrasonic wave reflected by the subject;
an image processor configured to convert ultrasonic image data based on the ultrasonic wave received by the probe, into digital data;
a main body configured to output the digital data output from the image processor;
a connector configured to electrically connect and disconnect the image processor with respect to the main body; and
an attaching/detaching mechanism configured to attach and detach a first housing with respect to a second housing, the attaching/detaching mechanism including paired elongated structures disposed on sides of the first housing and the second housing,
wherein the probe and the image processor are contained in the first housing, and
wherein the main body is contained in the second housing, and
wherein the attaching/detaching mechanism can be transitioned into:
a state where an electrical connection between the image processor and the main body via the connector is established, and the first housing is mechanically coupled with the second housing,
a state where the electrical connection between the image processor and the main body via the connector is cut off, and the first housing is mechanically decoupled from the second housing, and,
a state where the electrical connection between the image processor and the main body via the connector is cut off, and the first housing is mechanically coupled to the second housing, and
wherein when in the state where the electrical connection between the image processor and the main body via the connector is cut off, the first housing is mechanically coupled to the second housing by the attaching/detaching mechanism such that there is a gap between the first housing and the second housing.

4. An ultrasonic diagnostic system comprising:
an ultrasonic diagnostic device; and
a terminal device,
wherein the ultrasonic diagnostic device includes:
a probe configured to transmit an ultrasonic wave to a subject and to receive the ultrasonic wave reflected by the subject,
an image processor configured to convert ultrasonic image data based on the ultrasonic wave received by the probe, into digital data,
a main body configured to output the digital data output from the image processor, to the terminal device,
a connector configured to electrically connect and disconnect the image processor with respect to the main body, and
an attaching/detaching mechanism configured to attach and detach a first housing with respect to a second housing, the attaching/detaching mechanism including paired elongated structures disposed on sides of the first housing and the second housing,
wherein the probe and the image processor are contained in the first housing, and
wherein the main body is contained in the second housing, and
wherein the attaching/detaching mechanism can be transitioned into:
a state where an electrical connection between the image processor and the main body via the connector is established, and the first housing is mechanically coupled with the second housing,
a state where the electrical connection between the image processor and the main body via the connector is cut off, and the first housing is mechanically decoupled from the second housing, and
a state where the electrical connection between the image processor and the main body via the connector is cut off, and the first housing is mechanically coupled to the second housing,
wherein when in the state where the electrical connection between the image processor and the main body via the connector is cut off, the first housing is mechanically coupled to the second housing by the attaching/detaching mechanism such that there is a gap between the first housing and the second housing.

\* \* \* \* \*